United States Patent
Lacey et al.

(10) Patent No.: US 6,641,300 B1
(45) Date of Patent: Nov. 4, 2003

(54) DIFFERENTIAL SCANNING CALORIMETER

(75) Inventors: Andrew Lacey, Edinburgh (GB); Michael Reading, Leicester (GB)

(73) Assignee: Waters Investment, Ltd., New Castle, DE (US)

(*) Notice: Subject to any disclaimer, the term of this patent is extended or adjusted under 35 U.S.C. 154(b) by 69 days.

(21) Appl. No.: 10/058,025

(22) Filed: Jan. 29, 2002

Related U.S. Application Data

(60) Provisional application No. 60/264,311, filed on Jan. 29, 2001.

(51) Int. Cl.[7] .................. G01K 17/00; G01K 19/00; G01N 25/48
(52) U.S. Cl. .................. 374/31; 374/1; 374/43; 374/29
(58) Field of Search .................. 374/31, 32, 33, 374/10, 11, 1, 43, 29, 30

(56) References Cited

U.S. PATENT DOCUMENTS

| | | | |
|---|---|---|---|
| 3,263,484 A | 8/1966 | Watson et al. | |
| 3,732,722 A | 5/1973 | Norem et al. | |
| 4,095,453 A | 6/1978 | Woo | |
| 4,330,933 A | 5/1982 | Bullinger et al. | |
| 4,350,446 A | 9/1982 | Johnson | |
| 4,530,608 A | 7/1985 | O'Neill | |
| 4,614,721 A | 9/1986 | Goldberg | |
| 4,783,174 A | 11/1988 | Gmelin et al. | |
| 4,812,051 A | 3/1989 | Paulik et al. | |
| 5,033,866 A | 7/1991 | Kehl et al. | |
| 5,174,655 A | * 12/1992 | Litz et al. | 374/31 |
| 5,211,477 A | 5/1993 | Li | |
| 5,224,775 A | 7/1993 | Reading et al. | |
| 5,288,147 A | 2/1994 | Schaefer et al. | |
| 5,474,385 A | * 12/1995 | Reading | 374/33 |
| 5,549,387 A | * 8/1996 | Schawe et al. | 374/10 |
| 5,599,104 A | 2/1997 | Nakamura et al. | |
| 5,672,289 A | 9/1997 | O'Neill | |
| 5,813,763 A | 9/1998 | Plotnikov et al. | |
| 5,842,788 A | 12/1998 | Danley et al. | |
| 6,071,008 A | * 6/2000 | Hatta et al. | 374/31 |
| 6,079,873 A | 6/2000 | Cavicchi et al. | |
| 6,146,012 A | 11/2000 | Nakamura et al. | |
| 6,170,984 B1 | 1/2001 | Schawe et al. | |
| 6,200,022 B1 | 3/2001 | Hammiche et al. | |
| 6,390,669 B1 | 5/2002 | Nakamura et al. | |
| 6,551,835 B1 | * 4/2003 | Schawe et al. | 374/10 |

FOREIGN PATENT DOCUMENTS

| | | | | |
|---|---|---|---|---|
| DE | 3049105 A1 | * 7/1982 | | G01K/17/00 |
| EP | 645619 A2 | * 3/1995 | | G01N/25/48 |
| EP | 0 701 122 A1 | 3/1996 | | |
| WO | WO 95 33199 | 12/1995 | | |
| WO | WO 98 20314 A | 5/1998 | | |

OTHER PUBLICATIONS

"A Differential Scanning Calorimeter for Quantitative Differential Thermal Analysis," E.S. Watson and M.J. O'Neill, Analytical Chemistry, vol. 36, No. 7, pp. 1233–1238 (Jun. 1964).

(List continued on next page.)

*Primary Examiner*—Andrew H. Hirshfeld
*Assistant Examiner*—Stanley J. Pruchnic, Jr.
(74) *Attorney, Agent, or Firm*—Shaw Pittman LLP

(57) ABSTRACT

A method for calibrating thermal resistance and thermal capacitance parameters characterizing a DSC cell, and then calculating the heat flow to the sample based upon the results of the calibration. The method is applied in a conventional heat flux calorimeter, to obtain thermal analysis data having improved baseline and resolution. A first embodiment is based upon a model of a calorimeter in which there is no cross-talk between the sample and reference sides of a DSC cell. The thermal resistance and thermal capacitance parameters are calculated by carrying out a sequential series of calibration measurements with an empty DSC cell, materials on the reference side and materials on both the sample and reference sides. Another embodiment takes the existence of cross-talk between the sample and reference sides of the calorimeter into account.

20 Claims, 2 Drawing Sheets

OTHER PUBLICATIONS

"Diagnosis of Phase Shift in a Temperature–Modulated Calorimetric Method," Hatta et al., Journal of Thermal Analysis., vol. 4, pp. 577–584 (1998) (No Month).

"Differential Scanning Calorimetry an Introduction for Practitioners," G. Hohne, W. Hemminger and H.J. Flammersheim (Springer–Verlag, 1996), pp. 7–40 (No Month).

"Heat Capacity by Multi–Frequencies Sawtooth Modulation," B. Wunderlich, R. Androsch, M. Pyda and Y.K. Kwon, submitted to Thermochimica Acta, Sep. 1999, pp 181–190 (2000, No Month).

"Heat Capacity Measurement by Modulated DSC at Constant Temperature," A. Boller, Y. Jin, B. Wunderlich, Journal of Thermal Analysis, vol. 42 (1994), pp. 307–329 (No Month).

"High Precision Heat Capacity Measurement by Dynamic Differential Scanning Calorimetry," Hatta, et al., Jpn. J. Appl. Phys., vol. 35, L858–860 (Jul. 1996).

"The Analysis of Temperature Controlled Scanning Calorimeter," M.J. O'Neill, Analytical Chemistry, vol. 36, No. 7, pp. 1238–1245 (Jun. 1964).

* cited by examiner

DIFFERENTIAL SCANNING CALORIMETER

The present application claims priority from Provisional Patent Application No. 60/264,311, filed Jan. 29, 2001 which is incorporated by reference herein. The present application also incorporates by reference the following patent applications and patents: U.S. patent application Ser. No. 09/533,949 (the "'949 application"), entitled "Heat Flux Differential Scanning Calorimeter", filed Mar. 23, 2000 now abandoned; U.S. patent application Ser. No. 09/643,870 (the "'870 application"), entitled "Heat Flux Differential Scanning Calorimeter," filed Aug. 23, 2000 now U.S. Pat. No. 6,431,747 issued Aug. 13, 2002; U.S. patent Application Ser. No. 09/643,869 (the "'869 application"), entitled "Power Compensation Differential Scanning Calorimeter," filed Aug. 23, 2000 now U.S. Pat. No. 6,428,203 issued Aug. 6, 2002 U.S. patent application Ser. No. 09/767,903 (the "'903 application") entitled "Differential Scanning Calorimeter," filed Jan. 24, 2001 now U.S. Pat. No. 6,488,406 issued Dec. 3. 2002 and U.S. patent application Ser. No. 09/769,313 (the "'313" application), filed Jan. 26, 2001 now U.S. Pat. No. 6,561,692 issued May 13, 2002, entitled "Modulated Differential Scanning Calorimeter." These applications will be referred to collectively herein as the "T0 applications."

BACKGROUND

Differential Scanning Calorimeters (DSCs) measure the heat flow to a sample as the sample temperature is varied in a controlled manner. There are two basic types of DSCs, heat flux and power compensation. Brief descriptions of the two types of DSC are included below. A detailed description of the construction and theory of DSCs is disclosed in "Differential Scanning Calorimetry an Introduction for Practitioners", G. Höhne, W. Hemminger and H. -J. Flammersheim (Springer-Verlag, 1996).

Heat flux DSCs include a sensor to measure heat flow to a sample to be analyzed. The sensor has a sample position and a reference position. The sensor is installed in an oven whose temperature is varied dynamically according to a desired temperature program. As the oven is heated or cooled, the temperature difference between the sample and reference positions of the sensor is measured. This temperature difference is assumed to be proportional to the heat flow to the sample.

Power compensation DSCs include a sample and a reference holder installed in a constant temperature enclosure. Each of the holders has a heater and a temperature sensor. The average of the sample and reference holder temperatures is used to control temperature, which follows the desired temperature program. In addition, differential power proportional to the temperature difference between the holders is added to the average power to the sample holder and subtracted from the average power to the reference holder in an effort to reduce the temperature difference between sample and reference holders to zero. The differential power is assumed to be proportional to the sample heat flow and is obtained by measuring the temperature difference between the sample and reference holder. In commercial power compensation DSCs, the difference between sample and reference temperature is generally not zero because a proportional controller is used to control the differential power.

A sample to be analyzed is loaded into a pan and placed on the sample position of the DSC. An inert reference material may be loaded into a pan and placed on the reference position of the DSC, although usually the reference pan is empty. The temperature program for conventional DSCs typically includes combinations of linear temperature ramps and constant temperature segments. Modulated DSC (MDSC) uses a temperature program in which periodic temperature oscillations are superposed on linear ramps and isothermal segments. The experimental result is the sample heat flow versus temperature or time. The heat flow signal is the result of heat flow to or from the sample due to its specific heat and as a result of transitions occurring in the sample.

During the dynamic portion of the DSC experiment, a temperature difference is created between the sample and reference positions of the DSC. In heat flux DSCs, the temperature difference results from the combination of three differential heat flows: the difference between the sample and reference heat flow, the difference between sample and reference sensor heat flow and the difference between sample and reference pan heat flow. In power compensation DSCs, the temperature difference results from the combination of three differential heat flows plus the differential power supplied to the sample holders: the difference between the sample and reference heat flow, the difference between sample and reference holder heat flow and the difference between sample and reference pan heat flow. The heat flow difference between the sample and reference consists of heat flow due to the heat capacity difference between the sample and reference, the heat flow of a transition, or the difference in heating rate that occurs during an MDSC experiment. The heat flow difference between the sample and reference sections of the DSC is the result of thermal resistance and capacitance imbalances in the sensor or between the holders and the difference in heating rate that occurs between the sample and reference sections of the DSC during a transition or during an MDSC experiment. Similarly, the heat flow difference between the sample and reference pans is the result of mass differences between the pans and the difference in heating rate that occurs during a sample transition or during a MDSC experiment.

In conventional heat flux DSCs, the sensor imbalance and pan imbalance are assumed to be insignificant and the differences in heating rates are ignored. In conventional power compensation DSCs, the holder imbalance and pan imbalance are assumed to be insignificant and the differences in heating rates are ignored. When the balance assumptions are satisfied and the sample heating rate is the same as the programmed heating rate, the temperature difference is proportional to the sample heat flow and the differential temperature gives an accurate measure of the sample heat flow. The sample heat flow is only proportional to the measured temperature difference between the sample and reference when the heating rate of the sample and reference are identical, the sensor is perfectly symmetrical, and the pan masses are identical. Proportionality of sample heat flow to temperature difference for a balanced sensor and pans occurs only during portions of the experiment when the instrument is operating at a constant heating rate, the sample is changing temperature at the same rate as the instrument and there are no transitions occurring in the sample. During Modulated DSC experiments, the heating rates of the sample and reference are generally not the same and the difference between measured sample and reference temperatures is not proportional to the sample heat flow.

Thus, the sample heat flow from a conventional DSC is not the actual sample heat flow, but includes the effects of imbalances and differences in heating rates; in other words the DSC sample heat flow measurement is smeared. For many DSC experiments, the smeared sample heat flow is a sufficiently accurate result. For example, when the desired experimental result is the total energy of the transition, such as the heat of fusion of a melt, the total peak area is integrated over a suitable baseline and the result from a conventional DSC is sufficiently accurate. If, however, partial integration of the peak area is required (for example, in the study of reaction kinetics), the smeared sample heat flow of conventional DSC cannot be used. Another example of when the conventional DSC result is inadequate is when two or more transitions in a sample occur within a small temperature interval. In that case, the transitions may be poorly separated in prior art DSCs because of the smearing effects. The improvement in resolution of the present invention greatly improves the separation of closely spaced transitions. In any case, the heat flow signal from prior art DSCs does not accurately portray the sample heat flow during a transition.

During a transition, the heat flow to the sample increases or decreases from the pre-transition value depending upon whether the transition is endothermic or exothermic and whether the DSC is being heated or cooled. The change in sample heat flow causes the heating rate of the sample to be different from that of the DSC and as a consequence, the sample pan and sensor heating rates become different from the programmed heating rate.

U.S. patent applications Ser. Nos. 09/533,949 and 09/643,870, incorporated by reference above, disclose a heat flux DSC that uses a four term heat flow equation to account for sensor imbalances and differences in heating rate between the sample and reference sections of the sensor. The four term DSC heat flow equation derived in the '949 application is:

$$q = \Delta T_0 \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}$$

The first term accounts for the effect of the difference between the sensor sample thermal resistance and the sensor reference thermal resistance. The second term is the conventional DSC heat flow. The third term accounts for the effect of the difference between the sensor sample thermal capacitance and the sensor reference thermal capacitance. The fourth term accounts for the effect of the difference between the heating rates of the sample and reference sides of the DSC.

U.S. patent application Ser. No. 09/643,869, incorporated by reference above, discloses a power compensation DSC that uses a five term heat flow equation to account for sample and reference holder imbalances and differences in heating rate between the sample and reference holders. The five term power compensation DSC heat flow equation derived in the '869 application is:

$$q = \Delta p + \Delta T_0 \cdot \left(\frac{R_r - R_s}{R_r \cdot R_s}\right) - \frac{\Delta T}{R_r} + (C_r - C_s) \cdot \frac{dT_s}{d\tau} - C_r \cdot \frac{d\Delta T}{d\tau}$$

The first term is the difference in power supplied to the sample position versus the power supplied to the reference position. The second term accounts for differences between the thermal resistances of the sample and reference holders. The third term accounts for the heat flow that results from the difference in temperature between the sample and reference. The fourth term is the heat flow resulting from imbalances in thermal capacitance between the sample and reference holders. The fifth term reflects heat flow resulting from differences in heating rate between the sample and reference holders Heat flow results from the inventions disclosed in the T0 applications show improved dynamic response and hence improved resolution along with improvements in the DSC baseline heat flow.

GLOSSARY OF TERMS $R_s$ is the thermal resistance between the sample and the heat source (the "sample resistance");

$R_r$ is the thermal resistance between the reference and the heat source (the "reference resistance");

$C_s$, $C_r$ are the thermal capacitances of the sample and reference positions, respectively;

$C_{ps}$, $C_{pr}$ are the thermal capacitances of whatever is placed on the sample and reference position; typically, they will be the thermal capacitances of the sample and reference pans, respectively; however, if no pans are used, $C_{ps}$, $C_{pr}$ are the thermal capacitances of materials (such as sapphire) having known heat capacity that are placed on the sample and/or reference positions, respectively, without pans;

$R_{ps}$ is the thermal resistance between the sample pan and the sample sensor (the "sample pan resistance");

$R_{pr}$ is the thermal resistance between the reference pan and the reference sensor (the "reference pan resistance");

$R_c$ is the thermal resistance between the sample and reference positions;

$R_r^* = R_r/(1+(R_s+R_r)/R_c)$ is the composite reference resistance;

$R_s^* = R_s/(1+(R_s+R_r)/R_c)$ is the composite sample resistance;

$q_{ss}$ is the heat flow to the sample;

q is the differential heat flow to the sample position with respect to the reference position;

$C_{ss}$ is the heat capacity of the sample;

$T_s$ is the temperature of the sample position;

$T_r$ is the temperature of the reference position;

$T_d = T_s - T_r$;

$T_{ps}$ is the temperature of the sample pan;

$T_{pr}$ is the temperature of the reference pan; and

ω is the angular frequency of the modulation.

In the equations below, a bar above a quantity means its average over one period of modulation, or over integer multiples on one period of modulation. A ^over a quantity indicates that it is a complex quantity. Re and Im indicate the real and imaginary parts of a complex quantity, respectively.

SUMMARY OF THE INVENTION

The present invention is a method for calibrating the parameters characterizing a DSC cell, including sample and reference pans, and then calculating the heat flow to the sample based upon the results of the calibration. The cell parameters that are calibrated are $R_r$, $C_r$, $R_s$ and $C_s$, and the pan parameters are $R_{ps}$ and $R_{pr}$.

In A T0 Calorimeter

A T0 calorimeter is a calorimeter having the structure disclosed in the T0 applications referenced above. The notation used here is essentially the notation used in the T0 applications.

In the absence of any cross-talk, and assuming that the calorimeter can be thought of as having five parts—the base, the two thermocouples, and the two pans (including their contents), and also assuming that the temperature in each part is independent of position and that the heat transfer is between neighboring parts and is proportional to temperature difference, then the model is:

$$q_{ss} + C_{ps}\frac{dT_{ps}}{dt} + C_s\frac{dT_s}{dt} = \frac{1}{R_s}(T_0 - T_s), \quad (1)$$

$$q_{ss} + C_{ps}\frac{dT_{ps}}{dt} = \frac{1}{R_{ps}}(T_s - T_{ps}), \quad (2)$$

$$C_{pr}\frac{dT_{pr}}{dt} + C_r\frac{dT_r}{dt} = \frac{1}{R_r}(T_0 - T_r), \quad (3)$$

$$C_{pr}\frac{dT_{pr}}{dt} = \frac{1}{R_{pr}}(T_r - T_{pr}), \quad (4)$$

The heat capacity of the sample, $C_{ss}$, is related to the heat flow through $$q_{ss} = C_{ss}\frac{dT_{ps}}{dt}.$$

$T_{pr}$ is given, in principle, by (4) so:

$$C_{pr}\frac{dT_{pr}}{dt} = \frac{1}{R_{pr}}\left(T_r - \frac{1}{C_{pr}R_{pr}}\int^t e^{-(t-\tau)/C_{pr}R_{pr}}T_r(\tau)d\tau\right). \quad (5)$$

(The heat capacity $C_{pr}$ and thermal resistance $R_{pr}$ are here assumed to change only slowly when compared with the calorimeter-induced transients.)

In the expression for $q_{ss}$, it is assumed that the thermal resistance between the sample and the sample pan is negligible, so that their temperatures can be considered to be equal. Below, the same assumption will be made for the reference side, i.e., the thermal resistance between the reference and the reference pan will be assumed to be negligible, such that their temperatures can be considered to be equal.

In A Conventional DSC

The present invention obtains results in a conventional DSC that are quantitatively similar to results obtained using the methods disclosed in the T0 applications. It is also possible to measure all the required quantities ($R_r$, $R_s$, $C_r$, $C_s$, etc.) through calibration experiments without the need for the T0 thermocouple. Consequently, it is possible, in principle, to obtain the improved baseline and resolution that are the main advantages of the T0 approach without a T0 cell (the issue of cross-talk will be addressed below).

The inventions disclosed in the T0 applications have the advantage that the total calibration procedure is simpler and the reference pan can be changed without the need for recalibration. These are a significant benefits. However, calibration need not be performed often and it is standard practice to leave a reference pan unchanged for long periods of time.

The treatment given here is applied to heat-flux DSCs. Some consideration should also be given to whether there is an equivalent in power-compensation instruments.

In a conventional heat flux calorimeter, the combination $R_r \times (3) - R_s \times (1)$ (i.e., multiply equation (3) by $R_r$ and equation (1) by $R_s$, and subtract the latter result from the former result) can be used to obtain an expression (see equation 9a below) that is equivalent to the equation used in the '949 and '870 applications. For $T_d = T_r - T_s$ $$T_d + R_r C_r \frac{dT_d}{dt} - (R_s C_s - R_r C_r)\frac{dT_s}{dt} = \quad (6)$$

$$R_s q_{ss} + R_s C_{ps}\frac{dT_{ps}}{dt} - R_r C_{pr}\frac{dT_{pr}}{dt}$$

Here, as below, the first term on the left can be considered as equivalent to conventional DSC, the second terms corrects for transient behavior, while the last accounts for asymmetry.

DETAILED DESCRIPTION OF THE INVENTION

Figure 1:
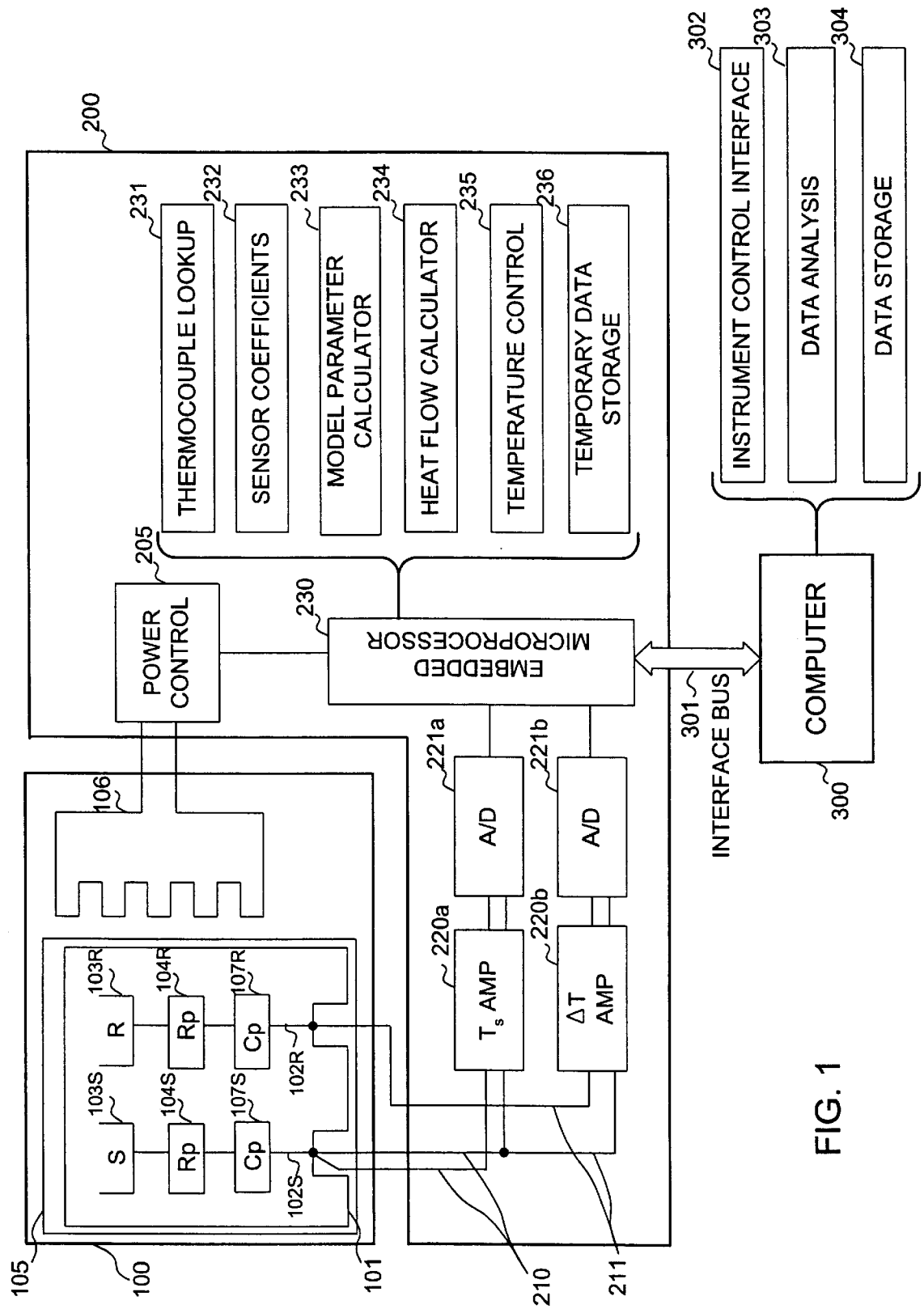
FIG. 1 is a schematic diagram representing a differential scanning calorimeter.

FIG. 1 is a schematic diagram representing a differential scanning calorimeter that can be used to practice the present invention. The differential scanning calorimeter comprises three main components, DSC cell 100, DSC module 200 and computer 300. DSC cell 100 comprises a sensor assembly 101 with sample position 102S and a reference position 102R. A sample within a sample pan 103S and a reference within a reference pan 103R are placed on the sample and reference positions. Heat is exchanged between each of the pans and its sensor position by a sample thermal contact thermal resistance 104S and heat capacity 107S and a reference thermal contact thermal resistance 104R and heat capacity 107R.

The sensor assembly is installed within an enclosure 105 heated by heating element 106. The temperature of the DSC cell is controlled via power control 205, according to instructions received from embedded microprocessor 230. The DSC module comprises $T_s$ and $\Delta T$ amplifiers 220a and 220b, respectively, which receive input from thermocouples 210 and 211 as shown in FIG. 1. The output signals of the $T_s$ and $\Delta T$ amplifiers are converted from analog to digital signals by A/D converters 221a and 221b. The output of the A/D converters is provided to embedded microprocessor 230. Embedded microprocessor 230 comprises thermocouple lookup application 231, sensor coefficient application 232, model parameter calculator 233, heat flow calculator 234, temperature control application 235 and temporary data storage 236.

Thermocouple Lookup 231 is a program resident in embedded microprocessor 230 that converts the digital signal representing the output signal of $T_s$ thermocouple 210 to a temperature. The temperature of the ends of the $T_s$ thermocouple wire is measured by a thermistor, and that temperature is converted to the equivalent voltage a thermocouple at that temperature. The equivalent thermocouple voltage is summed with the output voltage of $T_s$ thermocouple 210. The resultant reference junction compensated voltage is converted to temperature by using a table of temperature versus voltage based, for example, on NIST Monograph 175.

Sensor Coefficients 232 is a program resident in embedded microprocessor 230 that determines the sensor coefficients ($R_s$, $R_r$, $C_s$, $C_r$) used in the heat flow calculation. The temperature of the sample as indicated by $T_s$ thermocouple 210 is used to determine the appropriate value for each of the coefficients. Sensor coefficients are generated using the calibration procedures disclosed in the '949 and '870 applications and are saved in the module in tabular form. The program of sensor coefficients 232 supplies the sensor coefficients to the heat flow calculator.

Figure 2:
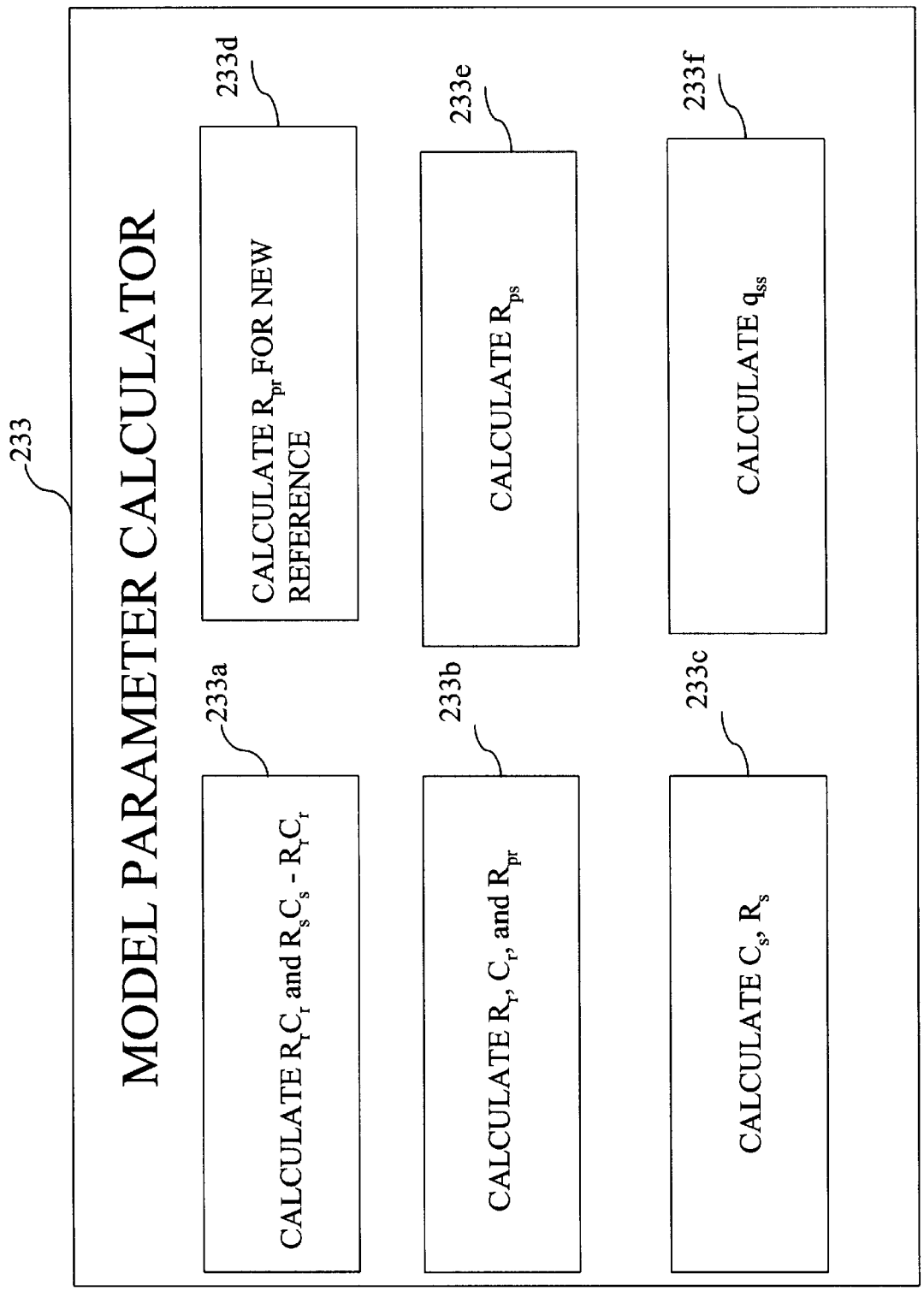
FIG. 2 is a schematic diagram illustrating the first embodiment of the invention.

Model Parameter Calculator 233 is a program resident in embedded microprocessor 230 that calculates the model parameters using the model equations described herein. FIG. 2 is a schematic diagram that illustrates the first embodiment of the invention, as explained below.

Heat Flow Calculator 234 is a program resident in embedded microprocessor 230 that calculates the heat flow using the methods described in the '949 and '870 applications. Sensor coefficients required by the program are supplied by the sensor coefficient program 232 and model parameters needed by the program are supplied by the model parameter calculator program 233.

Temperature Control 235 is a program resident in embedded microprocessor 230 that determines the power to be supplied to DSC heater 106. It implements a proportional plus integral plus derivative control algorithm.

Temporary Data Storage 236 is non-volatile RAM within module 200 that stores results of an experiment during the experiment.

Embedded microprocessor 230 is in communication over, e.g., an interface bus 301, with computer 300. Computer 300 includes instrument control interface 302, data analysis module 303, and data storage module 304.

Instrument Control Interface 302 is a program resident in computer 300 that provides the user interface to module 200. It is used to program the thermal method for the experiment, to select any options and control the instrument, e.g. start and stop experiments, to select purge gas flow rates, and to select instrument mode, MDSC or standard DSC.

Data Analysis 303 is a program resident in computer 300 that is used to display and process the results of the experiment. The user may select the signals to be displayed and display options such as axis scaling and selection of the abcissa. Analysis of the results may also be performed, such as integration of the area of a peak to determine the enthalpy of a transition. Data Storage 304 provides non-volatile storage of the experimental results, typically in a hard disk drive.

The present invention comprises a methodology that allows the important characteristics of the calorimeter to be quantified, so as to provide results that are equivalent to the results obtained using the procedures described in the T0 applications incorporated by reference above.

First Embodiment: A calorimeter with bias, No Cross-talk

The first embodiment of the invention is based upon a model of a conventional DSC in which there is a bias between the sample and the reference sides of the DSC cell, and there is no cross-talk between the sample and reference sides of the cell. In most cases, calorimeters have a bias, i.e., $C_r$ and $C_s$ are not the same and/or $R_r$ and $R_s$ are not the same, such that $R_rC_r$ differs from $R_sC_s$. In practice, there are almost no calorimeter cells that are so well balanced that there is no measurable bias.

Stage 1: No sample, no sample pan, no reference and no reference pan:

$(C_{ps}=C_{pr}=0; q_{ss}=0).$

The temperature of an empty DSC cell is increased at an underlying constant heating rate, with a superimposed modulation as described in the MDSC patent, U.S. Pat. No. 5,224,775. Because there is bias, the measured temperature difference $T_d$ is not zero. From the average heat flow signal (referred to as the "total" signal in the '775 patent) we can determine the quantity $R_sC_s-R_rC_r$ (which is a measure of the bias in the DSC cell):

$$R_sC_s - R_rC_r = \frac{\overline{T_d}}{b}$$

where b is the average temperature rise of $T_s$ and $T_r$.

From the amplitude of the modulation we can determine $R_rC_r$:

$$R_rC_r = \sqrt{(R_sC_s - R_rC_r)^2 \frac{|\hat{T}_s|^2}{|\hat{T}_d|^2} - \frac{1}{\omega^2}}$$

where: $|\hat{T}_s|$ is the amplitude of the cyclic part of $T_s$;

$|\hat{T}_d|$ is the amplitude of the cyclic part of $T_d$.

$R_rC_r$ can also be determined in other ways, for example using the phase lag between the reference heat flow signal and the reference temperature signal. Alternatively, $R_rC_r$ and $R_sC_s-R_rC_r$ can be determined as follows:

$$R_rC_r = \frac{\text{Re}\left\{\frac{\hat{T}_d}{\hat{T}_s}\right\}}{\omega \text{Im}\left\{\frac{\hat{T}_d}{\hat{T}_s}\right\}}$$

$$R_sC_s - R_rC_r = \frac{(1+\omega^2(R_rC_r)^2)\text{Im}\left\{\frac{\hat{T}_d}{\hat{T}_s}\right\}}{\omega}$$

where the cyclic parts of $T_d$ and $T_s$ are $\text{Re}\{\hat{T}_d e^{i\omega t}\}$ and $\text{Re}\{\hat{T}_s e^{i\omega t}\}$, respectively.

Stage 2: A reference pan or a calibration material on the reference side:

$(q_{ss}=0, C_{ps}=0, C_{pr}>0).$

For example, a calibration material having a known heat capacity, such as a sapphire disk, may be placed on the reference side without a pan. The sample side is empty, i.e., no sample and no sample pan. In this case, if a calibration material is used, $C_{pr}$ refers to the heat capacity of the calibration material. The temperature is ramped with modulation.

With a reference pan or calibration material that has a known heat capacity, $C_{pr}$ is known and:

$$-R_rC_{pr}\frac{dT_{pr}}{dt} = R_rC_r\frac{dT_d}{dt} + T_d - (R_sC_s - R_rC_r)\frac{dT_s}{dt}, \quad (7)$$

so further calibration can be used to obtain $R_r$. Because $R_rC_r$ is known from Stage 1, $R_{pr}C_{pr}$ and hence $R_{pr}$ (looking at the time constant associated with equation (4) and apparent in the right-hand side of equation (7) during a transient) can be obtained as follows:

$$R_r = \frac{(R_sC_s - R_rC_r) - \frac{\bar{T}_d}{b}}{C_{pr}}$$

$$R_{pr}C_{pr} = \text{Re}\left\{\frac{-R_rC_{pr}(\hat{T}_d + \hat{T}_s)}{(1 + i\omega R_rC_r)\hat{T}_d - i\omega(R_sC_s - R_rC_r)\hat{T}_s}\right\}$$

and:

$$R_{pr} = \text{Re}\left\{\frac{-R_r(\hat{T}_d + \hat{T}_s)}{(1 + i\omega R_rC_r)\hat{T}_d - i\omega(R_sC_s - R_rC_r)\hat{T}_s}\right\} \quad (8)$$

$R_{pr}$ may also be obtained from the amplitude only or from the phase only. Hence, $R_r$, $C_r$, $R_{pr}C_{pr}$, and $R_{pr}$ can all be determined.

Stage 3: Calibrating with a sample pan or a calibration material (such as a sapphire disk) having a known heat capacity on the sample side ($q_{ss}=0$, $C_{ps}>0$, $C_{pr}>0$).

The sample pan or calibration material is placed onto the sample side, and the DSC cell is ramped up at a constant heating rate without modulation. Both $C_{ps}$ and $C_{pr}$ are non-zero and known, and the average differential temperature signal $\bar{T}_d$ is measured. This enables $R_s$ to be determined from (6) ($q_{ss}=0$):

$$R_s = \frac{\bar{T}_d - (R_sC_s - R_rC_r)b + R_rC_{pr}b}{bC_{ps}}$$

With $R_s$ determined, $C_s$ can be calculated from $R_rC_r$ and $R_sC_s - R_rC_r$ (which were determined in Stage 1) and $R_s$. Thus, Stages 1, 2 and 3 enable the determination of $C_s$, $C_r$, $R_s$, $R_r$ and $R_{pr}$.

Stage 4

With bias, Stages 1–3 give the calorimeter's parameters $R_r$, $C_r$, $R_s$ and $C_s$, as well as $R_{pr}$ (for the reference pan used in the calibration). If a new set of experiments are to be done, they may use a different size reference, in which case $R_{pr}$ would likely need to be determined again. Stage 4 is then used to obtain $R_{pr}$ for the new reference.

A pan is placed on the reference side of the DSC cell, and its temperature is then increased at a constant rate with modulation. There are then two alternatives:

(a) We assume that the heat capacity of aluminum (the material of the pan) is well known, which means that $C_{pr}$ is also known. Equation (8) above can be applied again to get the new value for $R_{pr}$. Alternatively, $R_{pr}$ may also be obtained from the amplitude only or from the phase only.

(b) We assume that the heat capacity of the pan is not well known. In this case we obtain a value for the heat capacity from the average signal, $$C_{pr} = \frac{b(R_sC_s - R_rC_r) - \bar{T}_d}{R_rb},$$

and proceed as in the preceding subsection (a).

At this stage, the heat capacity and thermal resistance for the reference are stored, and assumed to remain unchanged in subsequent experiments.

Stage 5

A pan with a sample is placed on the sample side. We assume that the sample pan behaves in the same way as the reference pan with appropriate adjustment for any difference in mass. Modulation at the start of the experiment, in a temperature region in which there is no transition, using, for example, the method of Hatta (Hatta and Ad Muramatsu, "High precision heat capacity measurement by dynamic differential scanning calorimetry," Jpn. J. Appl. Phys., vol. 35, L858–860 (1996), and Hatta and Katayama, "Diagnosis of phase shift in a temperature-modulated calorimetric method," J. Thermal Anal., vol. 4,577–584 (1998)) (collectively, the "Hatta articles"; the Hatta articles are incorporated by reference herein and are attached hereto as an Appendix) gives the heat capacity of the pan and the sample (and thus sample) and thermal resistance between the pan and the sensor as follows, by substituting $$q_{ss} = C_{ss}\frac{dT_{ps}}{dt}$$

into equations (2) and (6). The cyclic parts of the temperatures are then given as $\text{Re}\{\hat{T}_d e^{i\omega t}\}$, $\text{Re}\{\hat{T}_{ps} e^{i\omega t}\}$, $\text{Re}\{\hat{T}_s e^{i\omega t}\}$, $\text{Re}\{\hat{T}_{pr} e^{i\omega t}\}$, and $\text{Re}\{\hat{T}_r e^{i\omega t}\}$. Re-writing equation (2) to give $\hat{T}_{ps}$ in terms of $\hat{T}_s$, and equation (4) to give $\hat{T}_{pr}$ in terms of $\hat{T}_r = \hat{T}_s + \hat{T}_d$, and substituting in equation (6) leads to a single, but complex equation, involving $$\frac{\hat{T}_d}{\hat{T}_s},$$

$C_{ss}+C_{ps}$, $R_{ps}$, the calibrated constants ($R_s$, $R_s$, $C_r$, $C_s$, $R_{pr}$) and $C_{pr}$:

$$\frac{i\omega R_s(C_{ss} + C_{ps})}{1 + i\omega R_{ps}(C_{ss} + C_{ps})} =$$

$$(1 + i\omega R_rC_r)\frac{\hat{T}_d}{\hat{T}_s} - i\omega(R_sC_s - R_rC_r) + i\omega R_rC_{pr}\left(1 + \frac{\hat{T}_d}{\hat{T}_s}\right)(1 + i\omega R_{pr}C_{pr})$$

The real and imaginary parts of this equation lead to:

$$R_{ps} = R_s \cdot \text{Re}\left\{\frac{1}{\alpha}\right\}, \quad C_{ss} = -C_{ps} - \frac{1}{\omega R_s \text{Im}\left\{\frac{1}{\alpha}\right\}},$$

where $$\alpha = (1 + i\omega R_rC_r)\frac{\hat{T}_d}{\hat{T}_s} - i\omega(R_sC_s - R_rC_r) + i\omega R_rC_{pr}\frac{1 + \frac{\hat{T}_d}{\hat{T}_s}}{1 + i\omega R_{pr}C_{pr}}.$$

In stages 3, 4 and 5, values for the thermal resistances between pans and sensors are determined. For best results, some relationship between pan-sensor thermal resistance and temperature should be used. The T0 applications incorporated by reference above disclose a relationship that can be applied once a value is either measured or assumed at a given temperature for a given type of pan. This relationship, combined with measurements of $R_{pr}$ (Stage 2 or Stage 4) and of $R_{ps}$ (Stage 5) at a specific temperature, can be used to give values of $R_{pr}$ and of $R_{ps}$ at other temperatures. Alternatively, $R_{pr}$ could be evaluated (Stage 2 or Stage 4) at a number of temperatures and $R_{ps}$ measured (Stage 5) when no transitions are occurring, and interpolation employed to obtain $R_{pr}$ and $R_p$, at intermediate temperatures.

Stage 6. The experiment: $q_{ss}$ is to be found.

This, using equations (6) and (2), is essentially the same as equations (1) and (2) when $T_0$ is employed.

The heat flow into the sample (and hence its heat capacity) are given by:

$$q_{ss} = \frac{1}{R_s}\left(T_d + R_r C_r \frac{dT_{pr}}{dt} + (R_r C_r - R_s C_s)\frac{dT_s}{dt} + R_r C_{pr}\frac{dT_{pr}}{dt}\right) - C_{ps}\frac{dT_{ps}}{dt} \quad (9)$$

with $$C_{pr}\frac{dT_{pr}}{dt}$$

given by equations (4) or (5) and $T_{ps}$ determined by equation (2):

$$T_{ps} = T_s + \frac{R_{ps}}{R_s}\left(T_d + R_r C_r \frac{dT_d}{dt} + (R_r C_r - R_s C_s)\frac{dT_s}{dt} + R_r C_{pr}\frac{dT_{pr}}{dt}\right). \quad (10)$$

After stages 1 to 5, all parameters in equations (9) and (10) are known, just as in the T0 applications. FIG. 2 is a schematic diagram showing the six calculations, 233a–233f corresponding to Stages 1–6, respectively, required to practice this embodiment.

Second Embodiment: A Calorimeter With Bias, no Cross-talk

In a second embodiment of the present invention, which can also be used for calorimeters with measurable bias and no cross-talk, only Stages 1, 2 and 3 are performed. In this embodiment, the parameters $C_s$, $C_r$, $R_s$, $R_r$ and $R_{pr}$ are determined as described above, and the heat flow to the sample is given by a three-term equation (which is similar to equation 9, with $C_{pr}$ and $C_{ps}$ set to zero):

$$q = \frac{1}{R_s}\left(T_d + R_r C_r \frac{dT_d}{dt} + (R_r C_r - R_s C_s)\frac{dT_s}{dt}\right) \quad (9a)$$

Thus, the second embodiment can be practiced using the three calculations shown in blocks 233a–233c, corresponding to Stages 1–3, respectively, of FIG. 2, and block 233f (except that in block 233f, q is calculated, instead of $q_{ss}$).

Third Embodiment: A Calorimeter With no Measurable Bias Over at Least Part of the Temperature Range: no Cross-talk Although, in reality, it is almost inconceivable that a DSC cell would not have some bias over a significant part of the temperature range, the approach described above could not be used with a DSC cell that has no bias. If there is bias over most of the temperature range, the 'missing' values could be readily obtained by interpolation or extrapolation, since the values of the parameters do not change drastically as a function of temperature. However, in cells with no measurable bias, the following steps must be taken:

Stage 1

The same as for stage 1 above, but now because the calorimeter has a zero bias over at least part of the temperature range, in that range, $C_r R_r = C_s R_s$, i.e., $C_r R_r - C_s R_s = 0$. Therefore, it is not possible to find values for $R_r C_r$ or $R_s C_s$ over the zero-bias temperature range, using the procedures of Stage 1 above for the case of calorimeters with bias. (The method of Stage 1 above, however, could be performed to obtain these values over the remainder of the temperature range.)

Stage 2

Place a calibration material such as sapphire on the reference and ramp its DSC cell with modulation. The average signal $\overline{T}_d$ gives $R_r$ (as before):

$$R_r = \frac{(R_s C_s - R_r C_r) - \dfrac{\overline{T}_d}{b}}{C_{pr}}$$

The amplitude and phase from the modulation are used to calculate the real and imaginary parts of the apparent complex heat capacity of the calibration material.

Writing the oscillatory parts of the temperatures as $\{\hat{T}_s e^{i\omega t}\}$ etc., equations (7) and (4) lead to:

$$i\omega[(R_s C_s - R_r C_r)(i\omega R_{pr}C_{pr}+1) - R_r C_{pr}]\hat{T}_s = [(i\omega R_r C_r+1)(i\omega R_{pr}C_{pr}+1) + i\omega R_r C_{pr}]\hat{T}_d$$

This can be rewritten as:

$$\omega^2(R_r C_r)(R_{pr}C_{pr}) + i\omega\left((R_s C_s - R_r C_r)\left(i\omega\frac{\hat{T}_s}{\hat{T}_d}\right) - 1\right)(R_{pr}C_{pr}) - \quad (11)$$

$$i\omega(R_r C_r) = 1 + i\omega R_r C_{pr} + \left(i\omega\frac{\hat{T}_s}{\hat{T}_d}\right)R_r C_{pr} - \left(i\omega\frac{\hat{T}_s}{\hat{T}_d}\right)(R_s C_s - R_r C_r).$$

In equation (11), $R_r$, $C_{pr}$, $(R_s C_s - R_r C_r)$, as well as $\omega$ and $$\frac{\hat{T}_s}{\hat{T}_d},$$

are known. The imaginary part allows determination of $R_r C_r$ as follows:

$$R_r C_r = (R_s C_s - R_r C_r)\operatorname{Re}\left\{\frac{\hat{T}_s}{\hat{T}_d}\right\} -$$

$$R_{pr}C_{pr}\left(1 + \omega(R_s C_s - R_r C_r)\operatorname{Im}\left\{\frac{\hat{T}_s}{\hat{T}_d}\right\}\right) - R_r C_{pr}\left(1 + \operatorname{Re}\left\{\frac{\hat{T}_s}{\hat{T}_d}\right\}\right)$$

so $R_r C_r$ can be found in terms of $R_{pr}C_{pr}$. Substituting this back into the real part of (11) gives a quadratic equation for $R_{pr}C_{pr}$:

$$\omega^2\left[(R_s C_s - R_r C_r)\cdot\operatorname{Re}\left\{\frac{\hat{T}_s}{\hat{T}_d}\right\} - R_r C_{pr}\left(1 + \operatorname{Re}\left\{\frac{\hat{T}_s}{\hat{T}_d}\right\}\right)\right] -$$

$$\left(1 + \omega\cdot(R_s C_s - R_r C_r)\cdot\operatorname{Im}\left\{\frac{\hat{T}_s}{\hat{T}_d}\right\}\right)\cdot R_{pr}C_{pr}\right]\cdot R_{pr}C_{pr} -$$

$$\omega^2(R_s C_s - R_r C_r)\cdot\operatorname{Re}\left\{\frac{\hat{T}_s}{\hat{T}_d}\right\}\cdot R_{pr}C_{pr} - 1 + \omega R_R C_{pr}\cdot\operatorname{Im}\left\{\frac{\hat{T}_s}{\hat{T}_d}\right\} +$$

$$\omega(R_s C_s - R_r C_r)\cdot\operatorname{Im}\left\{\frac{\hat{T}_s}{\hat{T}_d}\right\} = 0$$

This procedure does lead to two possible solutions, only one of which is correct for the purposes of the calibration. In order to select the right solution, it might be necessary to repeat the procedure with a different angular frequency ω, obtain a second quadratic equation, and choose the two solutions from the two equations that are closest to each other. In practice, the two solutions will likely not be exactly the same—they will differ somewhat due to experimental error, and/or due to imperfections in the model. The user can then either select the solution that was measured at the frequency that will be used in subsequent experiments, or average the two solutions. Either selection would be acceptable—the first is preferable if the difference between the two solutions is likely due more to imperfections in the model, and the second selection is preferable if the difference is likely due more to experimental error.

Alternatively, the correct solution can be selected on the basis that it is close to the known average time constant for this type of cell, in which case the use of a second modulated experiment described in the previous paragraph would not be necessary.

Stages 3–5

These stages are the same as those given above for the first embodiment.

Stage 6: Calculating the Heat Flow to the Sample.

Given that all quantities are now known through the calibration, the heat flow into the sample can be calculated using equation (9) above. This provides for correction for bias due to both differences in heat capacity and thermal resistance and also a transient term (which then improves resolution). This gives an equivalent result to the improved calculation disclosed in the U.S. patent applications incorporated by reference without the need for the additional thermocouple. The third embodiment can be practiced using the calculations shown in blocks 233a–233f of FIG. 2, except that blocks 233a and 233b are combined to find $R_r$, $C_r$, $R_{pr}$ and $R_sC_s-R_rC_r$.

Fourth Embodiment: Both Bias and Cross-talk

The fourth embodiment of the invention accounts for the existence of cross-talk between the sample side and the reference side of DSC cells with bias. In this model, the furnace is taken, in effect, to be at a temperature $T_0$. In this model, there is a thermal resistance between the sample and reference, such that temperature changes in one can directly influence the temperature in the other. The composite reference resistance $R_r^*=R_r/(1+(R_s-R_r)/R_c)$ and the composite sample resistance $R_{s^*=R_s}/(1+(R_s+R_r)/R_c)$ are used to find $R_s^*$, $R_r^*$, $C_r$ and to develop an expression, equation (17) below, that is equivalent to equation (6) above. This then means that the same calibration procedure described above can be used to determine the values of the R* parameters. Having done this, the heat flow into the sample is given by equations (18) and (19) below.

The T0 Calorimeter

The model for the thermal behavior of the device is taken to be exactly that used to develop equations (1)–(4) above, except that there is now a path for heat to travel directly from one calorimeter to the other. This means that an extra heat-transfer term must be included in the two principal equations. The revised model is then:

$$q_{ss} + C_{ps}\frac{dT_{ps}}{dt} + C_s\frac{dT_s}{dt} = \frac{1}{R_s}(T_0 - T_s) + \frac{1}{R_c}(T_r - T_s) \quad (12)$$

$$q_{ss} + C_{ps}\frac{dT_{ps}}{dt} = \frac{1}{R_{ps}}(T_s - T_{ps}) \quad (13)$$

$$C_{pr}\frac{dT_{pr}}{dt} + C_r\frac{dT_r}{dt} = \frac{1}{R_r}(T_0 - T_r) + \frac{1}{R_c}(T_s - T_r) \quad (14)$$

$$C_{pr}\frac{dT_{pr}}{dt} = \frac{1}{R_{pr}}(T_r - T_{pr}). \quad (15)$$

The new constant $R_c$ is the direct thermal resistance between the two thermocouples.

Without T0

The manipulations used in the first embodiment can also be used to eliminate T0 here:

$$R_sq_{ss} + R_sC_{ps}\frac{dT_{ps}}{dt} - R_rC_{pr}\frac{dT_{pr}}{dt} + (R_sC_s - R_rC_r)\frac{dT_s}{dt} - R_rC_r\frac{dT_d}{dt} = \left(1 + \frac{R_s+R_r}{R_c}\right)T_d \quad (16)$$

where $T_d = T_r - T_s$.

Dividing through (16) by $(1+(R_s+R_r)/R_c)$ leads to:

$$R_s^*q_{ss} + R_s^*C_{ps}\frac{dT_{ps}}{dt} - R_r^*C_{pr}\frac{dT_{pr}}{dt} + (R_s^*C_s - R_r^*C_r)\frac{dT_s}{dt} - R_r^*C_r\frac{dT_d}{dt} = T_d \quad (17)$$

Equation (17) is the same as equation (6) of the first embodiment (with the terms rearranged), with $R_r$, $R_s$ replaced by $R_r^*=R_r/(1+(R_s+R_r)/R_c)$ and $R^*_s=R_s/(1+(R_s+R_r)/R_c)$ respectively. Calibration can then be carried out using the same procedure as in the first embodiment to find $R_s$, $R_r$, $C_r$, and $R_{pr}$, ($C_{ps}$ and $C_{pr}$ are assumed known here).

Finally, $$q_{ss} = \frac{1}{R_s^*}\left(T_d + R_r^*C_r\frac{dT_d}{dt} + (R_r^*C_r - R_s^*C_s)\frac{dT_s}{dt} + R_r^*C_{pr}\frac{dT_{pr}}{dt}\right) - C_{ps}\frac{dT_{ps}}{dt} \quad (18)$$

with $$C_{pr}\frac{dT_{pr}}{dt}$$

obtained from equation (15) and $T_{ps}$ obtained from equation (13):

$$T_{ps} = T_s + \frac{R_{ps}}{R_s^*}\left(T_d + R_r^*C_r\frac{dT_d}{dt} + (R_r^*C_r - R_s^*C_s)\frac{dT_s}{dt} + R_r^*C_{pr}\frac{dT_{pr}}{dt}\right). \quad (19)$$

Once again, $R_{ps}$, needs to be found from an experiment and this can be done using modulation away from transitions, and interpolating as necessary. Once we have $R_s^*$ and $R_r^*$ in place of $R_s$ and $R_r$ for the equations representing a calorimeter without cross-talk, we proceed as above, with $R_s^*$ replacing $R_s$ and $R_r^*$ replacing $R_r$. It is important to note that $R_c$ does not need to be known in order to practice this embodiment of the invention.

The fourth embodiment can be practiced using the calculations shown in blocks 233a–233f of FIG. 2, except that the thermal resistances are replaced by the composite thermal resistances.

An alternative implementation of the fourth embodiment is similar to the second embodiment (i.e., stops after Stage 3), but (like the fourth embodiment) allows for cross-talk.

Use of Modulation

Temperature modulation can be used and the heat flow into the sample can be calculated using the equations disclosed above. Just as in the DSC disclosed in the '903 application, this alternative eliminates frequency dependence and provides more accurate heat capacity measurements.

In preferred embodiments of the invention, the above calculations for one or more of the above embodiments are incorporated into a software application that would take the experimenter through the various stages in the experiment and automatically calculate the necessary parameters as a function of temperature (except for the thermal resistance between sample pan and sensor where some relationship with temperature must be assumed). Although this procedure is certainly longer and more complicated than the comparable procedure described in the T0 applications, it need not be performed very often and the user will likely not be concerned by the degree of complexity of the automated calculation.

The foregoing disclosure of the preferred embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for calibrating a differential scanning calorimeter having a differential scanning calorimeter cell and having a temperature range for which the cell has a bias comprising:

(a) measuring the average beat flow signal he increasing the temperature of an empty differential scanning calorimeter cell according to a modulated temperature ramp and measuring the difference between the temperature of the sample position and the reference position and the temperature of the sample position;

(b) calculating the difference between the product of the sample resistance times the sample heat capacity and the product of the reference resistance times the reference heat capacity from the average heat flow signal;

(c) calculating the product of the reference resistance times the reference heat capacity from the amplitude-modulated temperatures of the cell positions;

(d) placing a material having a known heat capacity on a reference position in the differential scanning calorimeter, increasing the temperature of the differential scanning calorimeter cell according to a modulated temperature ramp and measuring the difference between the temperature of the sample position and the reference position and the temperature of the sample position;

(e) calculating the reference resistance, the reference pan resistance, the reference heat capacity, and the product of the reference pan resistance times the reference pan heat capacity from the difference between the temperature of the sample position and the reference position and from the temperature of the sample position; and (f) calculating the sample resistance according to the values calculated in steps (b), (c) and (e).

2. The method of claim 1, further comprising determining the reference pan heat capacity.

3. The method of claim 2, further comprising determining the sample pan resistance.

4. The method of claim 1, further comprising determining the sample pan resistance.

5. The method of claim 1, further comprising determining the heat flow to the sample.

6. A method for calibrating a differential scanning calorimeter having a temperature range for which the calorimeter has no bias comprising:

(a) measuring the average heat flow signal by increasing the temperature of an empty differential scanning calorimeter cell according to a modulated temperature ramp and measuring the difference between the temperature of the sample position and the reference position and the temperature of the sample position;

(b) calculating the difference between the product of the sample resistance times the sample position heat capacity and the product of the reference resistance times the reference position heat capacity in temperature ranges for which the calorimeter has a bias form the measured heat flow signal;

(c) placing a material having a known heat capacity on a reference position in the differential scanning calorimeter, increasing the temperature of the differential scanning calorimeter cell according to a modulated temperature ramp and measuring the difference between the temperature of the sample position and the reference position and the temperature of the sample position;

(d) calculating the reference resistance, the product of the reference resistance times the reference beat capacity and the product of the reference pan resistance times the reference pan heat capacity from the difference between the temperature of the sample position and the reference position and the temperature of the sample position; and (e) calculating the sample resistance according to the values calculated in step (b) and (d).

7. The method of claim 6, further comprising determining the reference pan heat capacity.

8. The method of claim 7, further comprising determining the sample pan resistance.

9. The method of claim 6, further comprising determining the sample pan resistance.

10. The method of claim 6, further comprising determining the heat flow to the sample.

11. A method for measuring heat flow to a sample in a differential scanning calorimeter having a bias between the sample and reference sides of the calorimeter comprising:

(a) calculating the bias in the calorimeter;

(b) calculating the reference resistance, the reference pan resistance, the reference position heat capacity, and the product of the reference pan resistance times the reference pan beat capacity;

(c) calculating The sample resistance; and (d) calculating the heat flow to the sample according to the values calculated in steps (a), (b), and (c).

12. The method of claim 11, further comprising determining the reference pan heat capacity.

13. The method of claim 12, further comprising determining the sample pan resistance.

14. The method of claim 11, further comprising determining the sample pan resistance.

15. The method of claim 11, further comprising determining the heat flow to the sample.

16. A method for calibrating a differential scanning calorimeter having a temperature range for which the calorimeter has a bias comprising:

(a) measuring the average heat flow signal by increasing the temperature of an empty differential scanning calorimeter cell according to a modulated temperature ramp and measuring the difference between the temperature of the sample position and the reference position and the temperature of the sample position;

(b) calculating the difference between the product of the composite sample resistanoe times the sample heat capacity and the product of the composite reference resistance times the reference heat capacity from the average beat flow signal;

(c) calculating the product of the composite reference resistance times the reference heat capacity from the amplitude-modulated temperatures of the sample and reference positions;

(d) placing a material having a known heat capacity on a reference position in The differential scanning calorimeter, increasing the temperature of the differential scanning calorimeter cell according to a modulated temperature ramp and measuring the difference between the temperature of the sample position and the reference position and the temperature of the sample position;

(e) calculating the composite reference resistance, the reference pan resistance, the reference heat capacity, and the product of the reference pan resistance times the reference pan heat capacity from the difference between the temperature of the sample position and the reference position and from the temperature of the sample position; and (f) calculating the composite sample resistance according to the values calculated in steps (b), (c), and (e).

17. The method of claim 16, further comprising determining the reference pan heat capacity.

18. The method of claim 17, further comprising determining the sample pan resistance.

19. The method of claim 16, further comprising determining the sample pan resistance.

20. The method of claim 16, further comprising determining the heat flow To the sample.

* * * * *